(12) United States Patent
Salese et al.

US010137062B2

(10) Patent No.: US 10,137,062 B2
(45) Date of Patent: Nov. 27, 2018

(54) DRY WIPE TO DECREASE FRIZZ, STATIC AND INCREASE SHINE ON HAIR AND AID IN PREVENTION OF REOCCURANCE OF STATIC AND FRIZZ

(71) Applicant: L'OREAL, Paris (FR)

(72) Inventors: Michelle Salese, Clark, NJ (US); Jolene Morris, Westfield, NJ (US); Chelsea Ali, Piscataway, NJ (US)

(73) Assignee: L'OREAL, Paris (FR)

( * ) Notice: Subject to any disclaimer, the term of this patent is extended or adjusted under 35 U.S.C. 154(b) by 29 days.

(21) Appl. No.: 14/361,159

(22) PCT Filed: Nov. 30, 2012

(86) PCT No.: PCT/US2012/067300
§ 371 (c)(1),
(2) Date: May 28, 2014

(87) PCT Pub. No.: WO2013/082430
PCT Pub. Date: Jun. 6, 2013

(65) Prior Publication Data
US 2015/0034116 A1     Feb. 5, 2015

Related U.S. Application Data

(60) Provisional application No. 61/565,840, filed on Dec. 1, 2011.

(51) Int. Cl.
| A61K 8/02 | (2006.01) |
| A61F 13/12 | (2006.01) |
| A61K 8/37 | (2006.01) |
| A61Q 5/00 | (2006.01) |
| A61K 8/92 | (2006.01) |
| A45D 19/16 | (2006.01) |
| A61Q 5/06 | (2006.01) |
| A61Q 5/12 | (2006.01) |
| B05D 1/02 | (2006.01) |
| B05D 1/18 | (2006.01) |
| B05D 3/02 | (2006.01) |
| B05D 3/04 | (2006.01) |
| A61K 8/31 | (2006.01) |
| A61K 8/34 | (2006.01) |
| A61K 8/41 | (2006.01) |
| A61K 8/60 | (2006.01) |
| A61K 8/73 | (2006.01) |

(52) U.S. Cl.
CPC ............ *A61K 8/0208* (2013.01); *A45D 19/16* (2013.01); *A61F 13/12* (2013.01); *A61K 8/31* (2013.01); *A61K 8/342* (2013.01); *A61K 8/37* (2013.01); *A61K 8/375* (2013.01); *A61K 8/416* (2013.01); *A61K 8/60* (2013.01); *A61K 8/73* (2013.01); *A61K 8/92* (2013.01); *A61K 8/922* (2013.01); *A61K 8/927* (2013.01); *A61Q 5/00* (2013.01); *A61Q 5/06* (2013.01); *A61Q 5/12* (2013.01); *B05D 1/02* (2013.01); *B05D 1/18* (2013.01); *B05D 3/0272* (2013.01); *B05D 3/0406* (2013.01); *A61K 2800/31* (2013.01); *A61K 2800/59* (2013.01); *A61K 2800/805* (2013.01)

(58) Field of Classification Search
None
See application file for complete search history.

(56) References Cited

U.S. PATENT DOCUMENTS

| 4,149,551 A | 4/1979 | Benjamin et al. |
| 6,395,701 B1 | 5/2002 | Connor et al. |
| 6,753,063 B1 | 6/2004 | Pung et al. |
| 8,557,269 B2 | 10/2013 | Kleinwaechter et al. |
| 2003/0022572 A1 | 1/2003 | Gott et al. |
| 2004/0081679 A1* | 4/2004 | Simon .................. A61K 8/0208 424/443 |
| 2004/0092185 A1 | 5/2004 | Grafe et al. |
| 2004/0198620 A1* | 10/2004 | Johansson ................ A61K 8/19 510/130 |
| 2006/0039956 A1 | 2/2006 | Hensen et al. |
| 2008/0076314 A1* | 3/2008 | Blanz ..................... A01N 25/34 442/327 |
| 2011/0033512 A1* | 2/2011 | Breyfogle .............. A61K 8/891 424/401 |

FOREIGN PATENT DOCUMENTS

| EP | 0047116 A2 | 3/1982 |
| EP | 1371379 A1 | 12/2003 |

(Continued)

OTHER PUBLICATIONS

Communication Pursuant to Rule 164(1) EPC with Supplementary Partial European Search Report, European Application No. 12854017.6.

(Continued)

*Primary Examiner* — Tigabu Kassa
(74) *Attorney, Agent, or Firm* — Polsinelli PC

(57) ABSTRACT

The disclosure relates to methods of reducing static on hair or a cloth material, reducing hair frizz and/or increasing shine on hair by wiping the hair or cloth material with a dry wipe product. The dry wipe product comprises a flexible substrate having a first side and a second side; and either an anhydrous composition, or an aqueous composition, disposed over the first and/or second side(s) of the flexible substrate. When hair or cloth material is wiped with a side of the dry wipe product having the anhydrous composition or the aqueous composition disposed thereon, the anhydrous composition or aqueous composition is transferred from the flexible substrate of the dry wipe product to the hair or cloth material. The anhydrous compositions and aqueous compositions of the instant disclosure reduce static on hair and/or cloth, reduce hair frizz and/or increase shine on hair. The dry wipe products of the instant disclosure are particularly beneficial for hair care because they are dry, portable, disposable, may be biodegradable, and comprise compositions that are safe for personal use.

15 Claims, No Drawings

(56) References Cited

FOREIGN PATENT DOCUMENTS

| EP | 1405634 A1 | 4/2004 |
|---|---|---|
| GB | 2022415 A | 12/1979 |
| WO | WO-9921532 A1 | 5/1999 |
| WO | WO-99/55303 A1 | 11/1999 |
| WO | WO-03/037292 A1 | 5/2003 |

OTHER PUBLICATIONS

International Search Report, PCT/US2012/067300.

* cited by examiner

DRY WIPE TO DECREASE FRIZZ, STATIC AND INCREASE SHINE ON HAIR AND AID IN PREVENTION OF REOCCURANCE OF STATIC AND FRIZZ

CROSS REFERENCE TO RELATED APPLICATIONS

This application is a national stage application (under 35 U.S.C. § 371) of PCT/US2012/067300, filed Nov. 30, 2012, which claims benefit of provisional application No. 61/565, 840, filed Dec. 1, 2011, the entire contents of all are hereby incorporated by reference.

TECHNICAL FIELD

The present disclosure relates to methods of reducing static on hair or a cloth material, reducing hair frizz and/or increasing shine on hair. More specifically, the instant disclosure relates to methods of reducing static on hair or cloth material, reducing hair frizz and/or increasing shine on hair by wiping the hair or cloth material with a dry wipe product.

BACKGROUND OF THE DISCLOSURE

When the amount of moisture in hair decreases due to weather conditions or exposure to high temperatures during styling processes, the hair gives up surface electrons more readily and develops a positive electrostatic charge. The positive charge of individual hair fibers causes the hair fibers to repel one another resulting in a "static flyaway" condition (i.e., frizzy hair). Loss of moisture in the hair also causes hair to become brittle and damaged resulting in less shiny and more unattractive hair. Hair is often exposed to dry weather conditions in arid regions and/or during the winter months. Furthermore, many styling processes utilize heat to drive out moisture in the hair in order to lock in a temporary style that persists until the hair reabsorbs moisture. Accordingly, a product that decreases frizz and static and increases shine in hair would be of benefit to hair care.

BRIEF SUMMARY OF THE DISCLOSURE

The disclosure relates to methods of reducing static on hair or a cloth material, reducing hair frizz and/or increasing shine on hair by wiping the hair or cloth material with a dry wipe product. The dry wipe product comprises a flexible substrate having a first side and a second side; and either an anhydrous composition, or an aqueous composition, disposed over one or both sides of the flexible substrate. When hair or cloth material is wiped with a side of the dry wipe product of the instant disclosure having either the anhydrous composition or the aqueous composition disposed thereon, the anhydrous composition or aqueous composition is transferred from the flexible substrate of the dry wipe product to the hair or cloth material. The anhydrous compositions and aqueous compositions of the instant disclosure reduce static on hair and/or cloth, reduce hair frizz and/or increase shine on hair. The dry wipe products of the instant disclosure are particularly beneficial for hair care because they are dry, portable, disposable, may be biodegradable, and comprise compositions that are safe for personal use.

DESCRIPTION OF BEST AND VARIOUS EMBODIMENTS OF DISCLOSURE

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The term "water-insoluble" means those compounds which are either completely or partially insoluble in water.

The term "biodegradable," as used herein, refers to materials that are capable of being broken down, especially into innocuous products, by the action of living things (such as microorganisms).

The term "cloth material," as used herein, includes any textile or fabric material. Fabric materials include items such as towels, sheets and clothing, accessories, stuffed animals, rugs, hats, gloves, outerwear and curtains.

As used herein, the expression "at least one," means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

The term "anhydrous," as used herein, is intended to mean that the composition is either completely free of unbound water or contains substantially no unbound water, such as, for example, no more than about 1% by weight, or no more than about 0.5% by weight, based on the weight of each composition.

A first aspect of the disclosure relates to a dry wipe product comprising:
  (a) a flexible substrate having a first side and a second side; and
  (b) an anhydrous composition comprising at least one wax and a solvent comprising a fatty ester and an ester oil, wherein the anhydrous composition is disposed over the first and/or second side(s) of the flexible substrate.

The dry wipe product typically comprises an anhydrous composition comprising ozokerite, a second wax other than ozokerite, and a solvent comprising the fatty ester that is isopropyl palmitate and the ester oil that is caprylic/capric triglyceride. The additional wax other than ozokerite is usually beeswax. The anhydrous composition according to the instant disclosure may be formulated so that it is biodegradable. In addition, the dry wipe product may also be biodegradable.

The dry wipe product may be formulated as a single-use or multi-use product. The flexible substrate of the instant disclosure is typically a wood-fiber sheet that is shaped in the form of a glove having a palm side (i.e., a first side) and a top side (i.e., a second side), or is a wood-fiber sheet that is in the form of a geometric shape (e.g., a square, rectangular, triangular, hexagonal, or trapezoidal shape). In addition, the flexible substrate is usually biodegradable. The wood-fiber sheets of the instant disclosure may be obtained, for example, from WausauPaper®.

When the flexible substrate is a wood-fiber sheet that is in the form of a geometric shape, the geometric shape is typically a rectangle. The rectangular flexible substrate typically has a first dimension that is at least about 2 inches, such as from about 2 inches to about 6.4 inches and a second dimension that is at least about 4 inches, such as from about 4 inches to about 9 inches. More typically, the rectangular flexible substrate has a first dimension of about 2 inches and a second dimension of about 4 inches, or has a first dimension of about 6.4 inches and a second dimension of about 9 inches. The rectangular flexible substrates of the instant disclosure are typically about as thick as a dryer sheet.

The anhydrous composition may be disposed evenly or unevenly on the first and/or second side(s) of the flexible substrate. More typically, the anhydrous composition is disposed on both the first and second sides of the flexible substrate. When the dry wipe product is intended to be used on hair, a total amount of about 0.1 to about 1.5 grams of the anhydrous composition is typically disposed on the first and/or second sides of the flexible substrate. More typically, a total amount of about 0.25 grams to about 1.0 grams of the anhydrous composition is disposed on the first and/or second sides of the flexible substrate. The amount of anhydrous composition that is used in the dry wipe products of the instant disclosure corresponds directly to the size of the flexible substrate employed. Thus, more anhydrous composition will be used on larger flexible substrates than on smaller flexible substrates.

When the dry wipe product of the instant disclosure is intended for use on a cloth material or hard surface, a total amount of about 0.1 grams to about 5 grams of the anhydrous composition is usually disposed on the first and/or second sides of the flexible substrate. More typically, a total amount of about 0.25 grams to about 2 grams of the anhydrous composition is disposed on the first and/or second sides of the flexible substrate. The anhydrous composition may be disposed evenly or unevenly on the first and/or second sides of the flexible substrate. In addition, the amount of anhydrous composition that is used in the dry wipe products of the instant disclosure corresponds directly to the size of the flexible substrate employed. Thus, more anhydrous composition will be used on larger flexible substrates than on smaller flexible substrates.

The anhydrous composition of the instant disclosure comprises at least one wax. Non-limiting examples of waxes that may be used in the anhydrous compositions of the instant disclosure include ozokerite, bayberry, jasmine wax, mimosa wax, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, ethylene homo- or copolymers, stearoxy dimethicone, dimethicone behenate, stearyl dimethicone, as well as synthetic homo- and copolymer waxes such as PVP/eicosene copolymer and PVP/hexadecene copolymer, and mixtures thereof.

When the anhydrous compositions of the instant disclosure comprise a wax having a low melting point (e.g., a melting point that is below about 50° Celsius), the anhydrous compositions will usually comprise at least one additional wax having a high melting point (e.g., a melting point that is above about 50° Celsius). If the anhydrous compositions of the instant disclosure comprise a wax having a high melting point, the composition may or may not comprise additional waxes having a high or low melting point. Typically, the wax used in the anhydrous compositions of the instant disclosure is biodegradable. Most typically, the anhydrous compositions of the instant disclosure comprise a mixture of beeswax and ozokerite.

The anhydrous composition typically comprises wax in an amount that is greater than 0 wt. % to about 50 wt. % wax. More typically, the anhydrous composition comprises about 5 wt. % to about 35 wt. % wax. Most typically, the anhydrous composition comprises about 10 wt. % to about 25 wt. % wax. The wt. %, in each case, is relative to the total weight of the anhydrous composition.

When the anhydrous compositions of the instant disclosure comprise ozokerite, the compositions typically comprise greater than 0 wt. % to about 25 wt. % ozokerite. More typically, the anhydrous compositions comprise 5 wt. % to about 15 wt. % ozokerite. The wt. %, in each case, is relative to the total weight of the anhydrous composition.

Also included in the anhydrous compositions is a solvent comprising a fatty ester and an ester oil. The fatty ester can for example be selected from those obtained from a linear or branched chain, saturated or unsaturated alcohol having from 1 to 24 carbon atoms and from a linear or branched chain fatty acid having from 3 to 24 carbon atoms. As fatty esters, 2-ethylhexyl caprate/caprylate (or octyl caprate/caprylate), ethyl laurate, butyl laurate, hexyl laurate, isohexyl laurate, isopropyl laurate, methyl myristate, ethyl myristate, butyl myristate, isobutyl myristate, isopropyl myristate, 2-octyl-dodecyl myristate, 2-ethylhexyl monococoate (or octyl monococoate), methyl palmitate, ethyl palmitate, isopropyl palmitate, isobutyl palmitate, 2-ethylhexyl palmitate (or octyl palmitate), butyl stearate, isopropyl stearate, isobutyl stearate, 2-ethylhexyl stearate (or octyl stearate), isopropyl isostearate, isocetyl stearate, isostearyl isostearate, 2-ethylhexyl pelargonate (or octyl pelargonate), 2-ethylhexyl hydroxy-stearate (or octyl hydroxystearate), decyl oleate, diisopropyl adipate, di-2-ethylhexyl adipate (or dioctyl adipate), diisocetyl adipate, 2-ethylhexyl succinate (or octyl succinate), diisopropyl sebacate, 2-ethylhexyl malate (or octyl malate), pentaerythritol caprate/caprylate, 2-ethylhexyl hexanoate (or octyl hexanoate), octyldodecyl octanoate, isodecyl neopentanoate, isostearyl neopentanoate, octyldodecyl neopentanoate, isononyl isononanoate, isotridecyl isononanoate, cetearyl isononanoate, isodecyl isononanoate, isotridecyl isononanoate, lauryl lactate, myristyl lactate, cetyl lactate, myristyl propionate, 2-ethylhexyl 2-ethylhexanoate (or octyl 2-ethylhexanoate), 2-ethylhexyl octanoate (or octyl octanoate), cetyl 2-ethylhexanoate, pentaerythritol tetraisostearate, isopropyl lauroyl sarcosinate (Eldew SL 205® from Unipex), dicaprylyl carbonate (Cetiol CC from Cognis), and the benzoates of $C_{12}$-$C_{15}$ fatty alcohols (Finsolv TN® from FINETEX) can be used. The fatty esters used in the anhydrous compositions of the instant disclosure are usually biodegradable. Most typically, isopropyl palmitate is used.

The amount of fatty ester that is typically used in the anhydrous compositions of the instant disclosure is greater than 0 wt. % to about 50 wt. %. More typically, the amount of fatty ester that is employed in the anhydrous compositions discussed herein is about 10 wt. % to about 25 wt. %. The wt. %, in each case, is relative to the total weight of the anhydrous composition.

In addition, non-limiting examples of ester oils that may be used as a solvent in the anhydrous compositions of the instant disclosure include mono-, di- and tri-esters of glycerol or caprylic/capric triglycerides. Synthetic ester oils which may be used include, but are not limited to, trimyristin, triolein, tristearin and glyceryl dilaurate. Glyceride fatty esters derived from peanut oil, sesame oil, avocado oil, coconut, cocoa butter, almond oil, safflower oil, corn oil, cotton seed oil, castor oil, hydrogenated castor oil, olive oil, jojoba oil, palm oil, soybean oil, wheat germ oil, linseed oil, and sunflower seed oil may also be employed in the anhydrous compositions of the instant disclosure. The anhydrous compositions of the instant disclosure usually comprise an ester oil that is biodegradable. Most typically, caprylic/capric triglyceride is used.

The amount of ester oil that is usually used in the anhydrous compositions of the instant disclosure is greater than 0 wt. % to about 50 wt. %. More typically, about 15 wt. % to about 35 wt. % of ester oil is used in the anhydrous compositions of the instant disclosure. The wt. %, in each case, is relative to the total weight of the anhydrous composition.

The anhydrous compositions of the instant disclosure may further comprise a natural oil or natural butter. Non-limiting examples of natural oils and natural butters that may be employed in the compositions of the instant disclosure include camellina oil, maringa oil, argan oil, lavendar oil, sweet almond oil, avocado oil, castor oil, olive oil, jojoba oil, sunflower oil, wheatgerm oil, sesame oil, groundnut oil, grapeseed oil, soybean oil, rapeseed oil, safflower oil, coconut oil, corn oil, hazelnut oil, shea butter, palm oil, apricot kernel oil and beauty-leaf oil. Usually, a biodegradable natural oil is used in the anhydrous compositions of the instant disclosure.

Fragrances may also be incorporated into the anhydrous compositions of the instant disclosure. Fragrances may be aldehydes, ketones, or oils obtained by extraction of natural substances or synthetically produced. Often, fragrances are accompanied by auxiliary materials, such as fixatives, extenders, stabilizers and solvents. The fragrances employed in the compositions of the instant disclosure are typically biodegradable.

The anhydrous compositions of the present disclosure may also include conditioning agents. The conditioning agents may also be chosen from amino acids, proteins, extracts, fats, oils, esters, transesters, hydrocarbons, quats, polyquats, zwitterionic surfactants, amphoteric surfactants, alcohols, polyols, humectants, alkanolamides, fatty acids, ketones, and mixtures thereof. Most typically, the conditioning agent is Brassicyl Isoleucinate Esylate—also known as Emulsense™- and commercially available from the supplier Inolex. Furthermore, the conditioning agents employed in the compositions of the instant disclosure are usually biodegradable.

Non-limiting examples of polyols that may be employed in the compositions of the instant disclosure include glycerol, sorbitol, propylene glycol, pentylene glycol, butylene glycol, propanediol, products of addition of ethylene oxide and $C_3$-$C_4$ alkylene oxide to a polyol such as glycerol such as for example polyoxybutylene polyoxyethylene polyoxypropylene glycerol, the 2-ethylhexyl ester of glycerol, caprylyl glycol and mixtures thereof.

In addition to the above ingredients, the anhydrous compositions may also comprise additional water-insoluble materials such as silicones, water-insoluble polymers, resins and latexes, and ceramides. Water-insoluble polymers and resins include but are not limited to those containing carboxyl moieties, such as acrylates and other carboxy polymers. Water-insoluble materials for use in the present disclosure include silicones ranging from low molecular weight fluids to high molecular weight gums; hydrocarbons such as mineral oil, petrolatum, paraffins, iso-paraffins, aromatic hydrocarbons, and the like; plant oils such as olive, avocado, coconut, and the like; fatty acids; fatty esters; fatty alcohols; and fatty waxes. The water-insoluble materials employed in compositions of the instant disclosure are usually biodegradable.

Solid fatty alcohols such as myristyl alcohol, cetyl alcohol, stearyl alcohol, cetearyl alcohol, arachidyl alcohol, behenyl alcohol, lignoceryl alcohol, ceryl alcohol and montanyl alcohol, and mixtures thereof may also be employed in the anhydrous compositions of the instant disclosure.

In some instances, it may be advantageous to include an emulsifier in the anhydrous compositions of the instant disclosure. Non-limiting examples of emulsifiers that may be utilized in the compositions of the instant disclosure include glyceryl stearate, glycol stearate, self-emulsifying waxes, emulsifying silicones, fatty alcohols, and fatty acids.

Amidoamines may also be employed in the anhydrous compositions of the instant disclosure. Amidoamines that may be employed in the instantly disclosed compositions include, but are not limited to oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

When the dry wipe product is intended for use on a cloth material, it may be advantageous to include a softener compound in the anhydrous composition of the instant disclosure. Non-limiting examples of softener compounds that may be employed in the anhydrous compositions of the instant disclosure include cationic, anionic, nonionic, or zwitterionic compounds. Cationic softening compounds include the cationic nitrogen-containing compounds such as quaternary ammonium compounds which have one or two straight-chain organic groups of at least eight carbon atoms. Typically, the cationic fabric conditioning agents have one or two such groups of from 12 to 22 carbon atoms.

When the dry wipe product is intended for use on a cloth material, it may also be advantageous to include a fabric conditioning agent, such as those agents typically used in dryer-added fabric softening articles, in the anhydrous compositions of the instant disclosure.

The anhydrous composition of the instant disclosure is typically made by solubilizing the wax and additional ingredients (if present) in the solvent comprising the fatty ester and ester oil.

A second aspect of the disclosure relates to a method of making the dry wipe product comprising a flexible substrate having a first side and second side; and the anhydrous composition described above, wherein the anhydrous composition is disposed over at least one of the first and second sides of the flexible substrate. The method comprises:
  (a) melting the anhydrous composition;
  (b) applying the melted anhydrous composition to the first and/or second side(s) of the flexible substrate; and
  (c) cooling the anhydrous composition.

The anhydrous composition is typically melted by heating the composition to a temperature of about 40° Celsius to about 90° Celsius. More typically, the anhydrous composition is heated to a temperature of about 50° Celsius to about 70° Celsius. The anhydrous composition is usually mixed continuously while it is heated to ensure uniform melting. In addition, the melted anhydrous composition is usually applied to the first and second sides of the flexible substrate.

A third aspect of the disclosure relates to a dry wipe product comprising:

(a) a flexible substrate having a first side and a second side; and
(b) an aqueous composition comprising water, a polysaccharide, a sugar, a fatty alcohol, a cationic surfactant, and at least one natural oil,
wherein the aqueous composition is disposed over at least one of the first and second side(s) of the flexible substrate.

The dry wipe product may be biodegradable. In addition, the aqueous compositions of the instant disclosure are usually biodegradable and the polysaccharide used in the aqueous compositions mentioned herein is typically carageenan. In addition, the sugar used in the aqueous compositions of the instant disclosure is typically glucose. The solvent employed in the aqueous compositions of the instant disclosure is usually a mixture of cetearyl alcohol (i.e., a fatty alcohol) and dipalmitoylethyl hydroxyethylmonium methosulfate (i.e., a cationic surfactant). Moreover, the aqueous compositions of the instant disclosure usually comprise olive oil as the natural oil.

The dry wipe product may be formulated as a single-use or multi-use product. The flexible substrate of the instant disclosure is typically a wood-fiber sheet that is shaped in the form of a glove having a palm side (i.e., a first side) and a top side (i.e., a second side), or is a wood-fiber sheet that is in the form of a geometric shape (e.g., a square, rectangular, triangular, hexagonal, or trapezoidal shape). The wood-fiber sheets of the instant disclosure may be obtained, for example, from WausauPaper®. In addition, the flexible substrate is usually biodegradable.

When the flexible substrate is a wood-fiber sheet that is in the form of a geometric shape, the geometric shape is typically a rectangle. The rectangular flexible substrate typically has a first dimension that is at least about 2 inches, such as from about 2 inches to about 6.4 inches and a second dimension that is at least about 4 inches, such as from about 4 inches to about 9 inches. More typically, the rectangular flexible substrate has a first dimension of about 2 inches and a second dimension of about 4 inches, or has a first dimension of about 6.4 inches and a second dimension of about 9 inches. The rectangular flexible substrates of the instant disclosure are typically about as thick as a dryer sheet.

The aqueous composition may be disposed evenly or unevenly on the first and/or second side(s) of the flexible substrate. More typically, the aqueous composition is disposed on both the first and second sides of the flexible substrate. When the dry wipe product is intended to be used on hair, a total amount of about 0.1 to about 1.5 grams of the aqueous composition is typically disposed on the first and/or second sides of the flexible substrate. More typically, a total amount of about 0.25 grams to about 1.0 grams of the aqueous composition is disposed on the first and/or second sides of the flexible substrate. The amount of aqueous composition that is used in the dry wipe products of the instant disclosure corresponds directly to the size of the flexible substrate employed. Thus, more aqueous composition will be used on larger flexible substrates than on smaller flexible substrates.

When the dry wipe product of the instant disclosure is intended for use on a cloth material or a hard surface, a total amount of about 0.1 grams to about 5 grams of the aqueous composition is usually disposed on the first and/or second sides of the flexible substrate. More typically, a total amount of about 0.25 grams to about 2 grams of the aqueous composition is disposed on the first and/or second sides of the flexible substrate. The aqueous composition may be disposed evenly or unevenly on the first and/or second sides of the flexible substrate. In addition, the amount of aqueous composition that is used in the dry wipe products of the instant disclosure corresponds directly to the size of the flexible substrate employed. Thus, more aqueous composition will be used on larger flexible substrates than on smaller flexible substrates.

The aqueous compositions of the instant disclosure typically comprise greater than 0 wt. % to about 99 wt. % water, and the water is usually deionized. More typically, the compositions comprise about 50 wt. % to about 99 wt. % water. Most typically, the aqueous compositions discussed herein comprise about 75 wt. % to about 99 wt. % water. The wt. % of water, in each case, is relative to the total weight of the aqueous composition when it is applied to the flexible substrate before the flexible substrate is dried.

The aqueous composition employed in the dry wipe products of the instant disclosure also comprise a polysaccharide. Non-limiting examples of polysaccharides that may be employed in the aqueous compositions discussed herein include galactans, galactomannans, glucomannans, and polyuronic acids. Suitable galactans are agar, agarose, carageenan, kappa carageenan, iota carageenan, and lambda carageenan. Non-limiting examples of suitable galactomannans are locust bean gum and guar. Non-limiting examples of glucans that may be used in the aqueous compositions of the instant disclosure are cellulose, starch, dextrans, pullulan, beta 1,3-glucans, chitin, xanthan, and tamarind. Glucomannans that may be employed in the aqueous compositions of the instant disclosure include, but are not limited to, konjac. In addition, non-limiting examples of polyuronic acids that may be used in the aqueous compositions discussed herein include algin, alginates, and pectins. The polysaccharides may be derivatized with various groups such as sulfate, carboxylate, and hydroxyl, provided that the resulting polysaccharide still retains water solubility. The polysaccharides used in the aqueous compositions of the instant disclosure are usually biodegradable. Moreover, the polysaccharide used in the aqueous compositions of the instant disclosure is most typically carageenan.

The aqueous compositions of the instant disclosure typically comprise about 0.01 wt. % to about 35 wt. % of a polysaccharide. More typically, the compositions discussed herein comprise about 0.01 wt. % to about 4 wt. % of a polysaccharide. Most typically, the aqueous compositions of the instant disclosure comprise about 0.01 wt. % to about 3 wt. % of a polysaccharide. The wt. %, in each case, is relative to the total weight of the aqueous composition after the aqueous composition has been applied to the flexible substrate and the dry wipe product has been dried.

In addition to water and a polysaccharide, the aqueous compositions of the instant disclosure also comprise a sugar. Non-limiting examples of sugars that may be used in the aqueous compositions of the instant disclosure include glucose, galactose, arabinose, rhamnose, mannose, xylose, fucose, anhydrogalactose, galacturonic acid, glucuronic acid, mannuronic acid, galactose sulfate, and anhydrogalactose sulfate. Most typically, the aqueous compositions of the instant disclosure comprise glucose. The sugar used in the aqueous compositions of the instant disclosure are typically biodegradable.

The aqueous compositions of the instant disclosure typically comprise about 0.01 wt. % to about 40 wt. % of a sugar. More typically, the compositions discussed herein comprise about 0.01 wt. % to about 10 wt. % of a sugar. Most typically, the aqueous compositions of the instant disclosure comprise about 1 wt. % to about 5 wt. % of a sugar. The wt. %, in each case, is relative to the total weight of the aqueous composition after the aqueous composition has been applied to the flexible substrate and the dry wipe product has been dried.

The aqueous compositions of the instant disclosure also comprise a mixture that comprises both a fatty alcohol and cationic surfactant. Fatty alcohols that may be used in the aqueous compositions discussed herein include myristyl alcohol, cetyl alcohol, stearyl alcohol, cetearyl alcohol, arachidyl alcohol, behenyl alcohol, lignoceryl alcohol, ceryl alcohol, montanyl alcohol, and mixtures thereof. Typically, the mixtures employed in the aqueous compositions of the instant disclosure comprise myristyl alcohol, cetyl alcohol, stearyl alcohol, cetearyl alcohol, behenyl alcohol, or mixtures thereof. The mixtures of the instantly disclosed aqueous compositions usually comprise a biodegradable fatty alcohol. Most typically, the mixtures employed in the compositions discussed herein comprise cetearyl alcohol.

Cationic surfactants that may be employed in the mixtures of the aqueous compositions of the instant disclosure include dimethyl dilauryl ammonium chloride, diethyl dilauryl ammonium chloride, dipropyl dilauryl ammonium chloride, dimethyl dipalmityl ammonium chloride, diethyl dipalmityl ammonium chloride, dipropyl dipalmityl ammonium chloride, dimethyl dicetyl ammonium chloride, diethyl dicetyl ammonium chloride, dipropyl dicetyl ammonium chloride, dimethyl distearyl ammonium chloride, diethyl distearyl ammonium chloride, dipropyl distearyl ammonium chloride, dimethyl dibehenyl ammonium chloride, diethyl dibehenyl ammonium chloride, dipropyl dibehenyl ammonium chloride, distearoylethyl dimonium chloride, dipalmitoylethyldimonium chloride, distearoylethyl hydroxy ethylmonium methosulfate, and dipalmitoylethyl hydroxyethylmonium methosulfate. The cationic surfactant used in the aqueous compositions of the instant disclosure is usually biodegradable. Most typically, dipalmitoylethyl hydroxyethylmonium methosulfate is used in the mixtures of the instantly disclosed aqueous compositions.

The aqueous compositions of the instant disclosure typically comprise greater than 0 wt. % to about 20 wt. % of a mixture comprising both a fatty alcohol and cationic surfactant. More typically, the compositions discussed herein comprise about 0.01 wt. % to about 10 wt. % of a fatty alcohol/cationic surfactant mixture. The wt. %, in each case, is relative to the total weight of the aqueous composition after the aqueous composition has been applied to the flexible substrate and the dry wipe product has been dried.

The aqueous compositions of the instant disclosure also comprise at least one natural oil. Non-limiting examples of natural oils that may be employed in the compositions of the instant disclosure include camellina oil, maringa oil, argan oil, lavendar oil, sweet almond oil, avocado oil, castor oil, olive oil, jojoba oil, sunflower oil, wheatgerm oil, sesame oil, groundnut oil, grapeseed oil, soybean oil, rapeseed oil, safflower oil, coconut oil, corn oil, hazelnut oil, palm oil, apricot kernel oil and beauty-leaf oil. The compositions may also include a natural butter such as shea butter. The aqueous compositions of the instant disclosure typically comprise a biodegradable natural oil. The natural oil that is most typically used in the aqueous compositions discussed herein is olive oil.

The aqueous compositions of the instant disclosure typically comprise greater than 0 wt. % to about 20 wt. % natural oils and/or natural butters. More typically, the compositions discussed herein comprise about 0.01 wt. % to about 10 wt. % natural oils and/or natural butters. The wt. %, in each case, is relative to the total weight of the aqueous composition after the aqueous composition has been applied to the flexible substrate and the dry wipe product has been dried.

Fragrances may also be incorporated into the aqueous compositions of the instant disclosure. Fragrances may be aldehydes, ketones, or oils obtained by extraction of natural substances or synthetically produced. Often, fragrances are accompanied by auxiliary materials, such as fixatives, extenders, stabilizers and solvents. The fragrances employed in the compositions of the instant disclosure are typically biodegradable.

The aqueous compositions of the present disclosure may also include conditioning agents. The conditioning agents may also be chosen from amino acids, proteins, extracts, fats, oils, esters, transesters, hydrocarbons, quats, polyquats, zwitterionic surfactants, amphoteric surfactants, alcohols, polyols, humectants, alkanolamides, fatty acids, ketones, and mixtures thereof. Most typically, the conditioning agents employed in the compositions of the instant disclosure are biodegradable.

Non-limiting examples of polyols that may be employed in the compositions of the instant disclosure include glycerol, sorbitol, propylene glycol, pentylene glycol, butylene glycol, propanediol, products of addition of ethylene oxide and $C_3$-$C_4$ alkylene oxide to a polyol such as glycerol such as for example polyoxybutylene polyoxyethylene polyoxypropylene glycerol, the 2-ethylhexyl ester of glycerol, caprylyl glycol and mixtures thereof.

In addition to the above ingredients, the aqueous compositions may also comprise additional water-insoluble materials such as silicones, water-insoluble polymers, resins and latexes, and ceramides. Water-insoluble polymers and resins include but are not limited to those containing carboxyl moieties, such as acrylates and other carboxy polymers. Water-insoluble materials for use in the present invention include silicones ranging from low molecular weight fluids to high molecular weight gums; hydrocarbons such as mineral oil, petrolatum, paraffins, iso-paraffins, aromatic hydrocarbons, and the like; plant oils such as olive, avocado, coconut, and the like; fatty acids; fatty esters; fatty alcohols; and fatty waxes. The water-insoluble materials employed in compositions of the instant disclosure are usually biodegradable.

The aqueous compositions of the instant disclosure may also comprise preserving agents. Non-limiting examples of preserving agents that may be utilized in the instantly disclosed compositions include para-hydroxybenzoic acid esters (i.e., parabens such as methyl paraben, ethyl paraben and propyl paraben), phenoxyethanol, chlorhexidine digluconate, sodium benzoate, caprylyl glycol, iodopropynyl butyl carbamate, pentylene glycol, alkyltrimethylammonium bromides such as myristyltrimethylammonium bromide, dodecyltrimethylammonium bromide, hexadecyltrimethylammonium bromide, and mixtures thereof.

Furthermore, in addition to water, the aqueous compositions discussed herein may comprise solvents such as $C_1$-$C_4$ lower alkanols (e.g., ethanol or isopropanol), polyols and polyol ethers (e.g., 2-butoxyethanol, propylene glycol, propylene glycol monomethyl ether, diethylene glycol monoethyl ether and monomethyl ether), aromatic alcohols (e.g., benzyl alcohol or phenoxyethanol), isododecane, and mixtures thereof.

When the dry wipe product is intended for use on a cloth material, it may be advantageous to include a softener compound in the aqueous composition of the instant disclosure. Non-limiting examples of softener compounds that may be employed in the aqueous compositions of the instant disclosure include cationic, anionic, nonionic, or zwitterionic compounds. Cationic softening compounds include the cationic nitrogen-containing compounds such as quaternary ammonium compounds which have one or two straight-chain organic groups of at least eight carbon atoms. Typically, the cationic fabric conditioning agents have one or two such groups of from 12 to 22 carbon atoms.

When the dry wipe product is intended for use on a cloth material, it may also be advantageous to include a fabric conditioning agent, such as those agents typically used in dryer-added fabric softening articles, in the anhydrous compositions of the instant disclosure.

The aqueous composition of the instant disclosure is typically made by mixing the water, polysaccharide, sugar, fatty alcohol and cationic surfactant, and the at least one natural oil together. Alternatively, the aqueous composition of the instant disclosure can be made by solubilizing the water-insoluble materials of the composition (e.g., the olive oil, any additional water-insoluble materials, natural oils and/or natural butters) in the fatty alcohol and then mixing the solubilized mixture with the remaining ingredients of the aqueous composition.

A fourth aspect of the disclosure relates to a method of making the dry wipe product comprising a flexible substrate having a first side and second side; and the aqueous composition described above, wherein the aqueous composition is disposed over at least one of the first and second sides of the flexible substrate. The method comprises:
  (a) Spraying the aqueous composition on the first and/or second sides of the flexible substrate; and
  (b) Drying the flexible substrate.

Drying is typically accomplished using either a forced air drying method or by heating the flexible substrate, for example, in an oven. In addition, the aqueous composition is typically sprayed on both the first side and second side of the flexible substrate.

Yet another aspect of the disclosure relates to a method of making the dry wipe product comprising a flexible substrate having a first side and second side; and the aqueous composition described above, wherein the aqueous composition is disposed over at least one of the first and second sides of the flexible substrate, wherein the method comprises:
  (a) Submerging the first side and/or second side of the flexible substrate in the aqueous composition;
  (b) Removing the flexible substrate from the aqueous composition; and
  (c) Drying the flexible substrate.

Drying is typically accomplished using either a forced air drying method or by heating the flexible substrate, for example, in an oven. Furthermore, both the first side and second side of the flexible substrate are usually submerged in the aqueous composition.

A sixth aspect of the disclosure relates to a dry wipe product as provided herein, wherein the dry wipe product is coupled with an applicator that is compatible with the dry wipe product. Such applicators may include a hair or cloth brush, a comb, a rod, or any other device that may be coupled with the dry wipe products of the instant disclosure in a manner that allows the anhydrous composition or aqueous composition to be wiped onto hair or a cloth material.

Another aspect of the disclosure relates to the anhydrous compositions and aqueous compositions described herein.

Yet another aspect of the disclosure relates to a method of reducing frizz, reducing static and/or increasing shine on hair comprising wiping the hair with a dry wipe product according to the instant disclosure. When the hair is wiped with a side of the dry wipe product having the anhydrous composition or the aqueous composition disposed thereon, the anhydrous composition or aqueous composition is transferred from the flexible substrate of the dry wipe product to the hair. Without being bound by any theory, it is likely that when a person holds the dry wipe product of the instant disclosure, and wipes the hair with the product, the heat from the person's hand aids in the transfer of the composition from the flexible substrate to the hair.

The compositions of the instant disclosure remain effective for a longer period of time (i.e., they are more durable) when they are applied to the hair using the dry wipe product described herein than when they are applied directly to the hair. Without being bound by any theory, it is believed that the compositions of the instant disclosure are effective for a longer period of time because the dry wipe product of the instant disclosure provides for a more uniform application of the compositions to the hair.

Another aspect of the disclosure relates to a method of reducing static on a cloth material comprising wiping the cloth material with a dry wipe product according to the instant disclosure. For instance, a user of the dry wipe product according to the instant disclosure could use the dry wipe product—which is portable—to reduce static on a cloth material that is in direct contact with another cloth material (e.g., a skirt that is in contact with pantyhose). When the cloth material is wiped with a side of the dry wipe product having the anhydrous composition or the aqueous composition disposed thereon, the anhydrous composition or aqueous composition is transferred from the flexible substrate of the dry wipe product to the cloth material. Without being bound by any theory, it is likely that when a person holds the dry wipe product of the instant disclosure and wipes the cloth material with the product, the heat from the person's hand aids in the transfer of the composition from the flexible substrate to the cloth material.

Yet another aspect of the disclosure relates to a method of increasing shine on a hard surface comprising wiping the hard surface with a dry wipe product according to the instant disclosure. When the hard surface is wiped with a side of the dry wipe product having the anhydrous composition or the aqueous composition disposed thereon, the anhydrous composition or aqueous composition is transferred from the flexible substrate of the dry wipe product to the hard surface. Without being bound by any theory, it is likely that when a person holds the dry wipe product of the instant disclosure, and wipes the hard surface with the product, the heat from the person's hand aids in the transfer of the composition from the flexible substrate to the hard surface.

When the dry wipe products of the instant disclosure are used for increasing shine on a hard surface, the anhydrous composition or aqueous composition disposed on the first and/or second side(s) of the dry wipe product may further comprise a surfactant. Non-limiting examples of surfactants that may be used in the compositions of the instant disclosure include a) nonionic surface-active agents with a hydrophilic-lipophilic balance (i.e., "HLB") of greater than or equal to 8 at 25° Celsius; b) nonionic surface-active agents with an HLB of less than 8 at 25° Celsius, optionally in combination with one or more nonionic surface-active agents with an HLB of greater than 8 at 25° Celsius; and c) anionic surfactants.

The anhydrous and aqueous compositions of the present disclosure will be illustrated further by the following non-limiting examples.

Example 1

Anhydrous Composition #1

| | |
|---|---|
| Isopropyl Palmitate | 15.00 grams |
| Beeswax | 18.00 grams |
| Dicaprylyl Carbonate | 6.00 grams |
| Stearyl Alcohol | 3.00 grams |
| Propanediol | 10.00 grams |
| Glyceryl Stearate SE | 6.00 grams |
| Ozokerite | 10.00 grams |
| Caprylic/Capric Trigyceride | 24.90 grams |
| Diisopropyl Adipate | 6.00 grams |
| Stearamidopropyl Dimethylamine | 0.50 grams |
| Olive Oil | 0.50 grams |
| Lavender Oil | 0.10 grams |

The anhydrous composition was made by solubilizing the beeswax, dicaprylyl carbonate, stearyl alcohol, propanediol, glyceryl stearate, ozokerite, diisopropyl adipate, stearamidopropyl dimethylamine, olive oil and lavendar oil in the solvent comprising isopropyl palmitate and caprylic/capric trigyceride. The solubilized mixture was then placed in a mixing vessel and heated while the contents of the mixing vessel were continuously stirred.

Example 2

Anhydrous Composition #2

| | |
|---|---|
| Isopropyl Palmitate | 15.00 grams |
| Beeswax | 18.00 grams |
| Dicaprylyl Carbonate | 6.00 grams |
| Stearyl Alcohol | 3.00 grams |
| Propanediol | 10.00 grams |
| Glyceryl Stearate SE | 6.00 grams |
| Ozokerite | 10.00 grams |
| Caprylic/Capric Triglyceride | 25.40 grams |
| Diisopropyl Adipate | 6.00 grams |
| Stearamidopropyl Dimethylamine | 0.50 grams |
| Lavender Oil | 0.10 grams |

The anhydrous composition was made by solubilizing the beeswax, dicaprylyl carbonate, stearyl alcohol, propanediol, glyceryl stearate, ozokerite, diisopropyl adipate, stearamidopropyl dimethylamine, and lavendar oil in the solvent comprising isopropyl palmitate and caprylic/capric trigyceride.

Example 3

Aqueous Composition

| | |
|---|---|
| Deionized Water | 438.75 grams |
| Chondrus Crispus (Carageenan) | 10.00 grams |
| Sodium Benzoate | 2.50 grams |
| Glucose | 15.00 grams |
| Cetearyl Alcohol (70% or 1.75 grams) and Dipalmitoylethyl Hydroxyethylmonium Methosulfate (30% or 0.75 grams) | 2.50 grams |
| Denatured Alcohol | 24.00 grams |
| Lavender Oil | 1.00 grams |
| Olive Oil | 1.25 grams |
| Benzyl Alcohol | 5.00 grams |

The aqueous composition was made by solubilizing the lavendar oil and olive oil in cetearyl alcohol, and then adding the solubilized oils to a mixture of the deionized water, carageenan, sodium benzoate, glucose, dipalmitoylethyl hydroxyethylmonium methosulfate, denatured alcohol and benzyl alcohol.

Illustrative Embodiments of the Invention

In the following paragraphs, illustrative embodiments of the present invention are identified by embodiment numbers for easy reference.

1. An anhydrous composition comprising:
   a. from about 5 wt. % to about 15 wt. % ozokerite; and
   b. from about 10 wt. % to about 25 wt. % of a fatty ester; and
   c. from about 15 wt. % to about 35 wt. % of an ester oil; and
   d. optionally, a second wax.

2. The anhydrous composition according to embodiment 1, wherein the fatty ester is isopropyl palmitate and the ester oil is caprylic/capric triglyceride.

3. The anhydrous composition according to embodiment 1 or 2, wherein the second wax is selected from the group consisting of bayberry, jasmine wax, mimosa wax, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, ethylene homo- or copolymers, stearoxy dimethicone, dimethicone behenate, stearyl dimethicone, synthetic homo- and copolymer waxes, and mixtures thereof.

4. The anhydrous composition according to any of embodiments 1-3, wherein the composition is biodegradable.

5. A dry wipe product comprising:
   a. a flexible substrate having a first side and a second side; and
   b. the anhydrous composition according to any of embodiments 1-4,
wherein the anhydrous composition is disposed over the first and/or second side(s) of the flexible substrate.

6. The dry wipe product according to embodiment 5, wherein the flexible substrate is biodegradable.

7. The dry wipe product according to embodiments 5 or 6, wherein the anhydrous composition further comprises at least one additional ingredient selected from the group consisting of:
   a. a natural oil or natural butter;
   b. a fragrance; and
   c. a conditioning agent,
wherein the at least one additional ingredient is biodegradable.

8. The dry wipe product according to any of embodiments 5-7, wherein the flexible substrate is rectangular and has a first dimension that is at least about 2 inches to about 6.4 inches and a second dimension that is at least about 4 inches to about 9 inches.

9. The dry wipe product according to embodiment 8, wherein the first dimension of the flexible substrate is about 2 inches and the second dimension of the flexible substrate is about 4 inches.

10. The dry wipe product according to embodiment 8, wherein the first dimension of the flexible substrate is about 6.4 inches and the second dimension of the flexible substrate is about 9 inches.

11. The dry wipe product according to any of embodiments 5-10, wherein the flexible substrate is a wood-fiber sheet.

12. The dry wipe product according to any of embodiments 5-11, wherein a total amount of about 0.1 grams to about 1.5 grams of the anhydrous composition is disposed on the first and/or second side(s) of the flexible substrate.

13. A method of reducing frizz, reducing static and/or increasing shine on hair comprising wiping the hair with the dry wipe product according to any of embodiments 5-12, wherein the hair is wiped with a side of the dry wipe product having the anhydrous composition disposed thereon.

14. A method of making the dry wipe product according to any of embodiments 5-12, comprising:
    a. melting the anhydrous composition;
    b. applying the melted anhydrous composition to the first and/or second side(s) of the flexible substrate; and
    c. cooling the anhydrous composition.

15. An aqueous composition comprising:
    a. water;
    b. from about 0.01 wt. % to about 1 wt. % of a polysaccharide;
    c. from about 0.01 wt. % to about 1 wt. % of a sugar;
    d. a fatty alcohol;
    e. a cationic surfactant; and
    f. from about 0.001 wt. % to about 0.010 wt. % of at least one natural oil.

16. The aqueous composition according to embodiment 15, wherein the polysaccharide is carageenan and the sugar is glucose.

17. The aqueous composition according to embodiment 15 or 16, wherein the fatty alcohol is cetearyl alcohol and the cationic surfactant is dipalmitoylethyl hydroxyethylmonium methosulfate.

18. A dry wipe product comprising:
    a. a flexible substrate having a first side and a second side; and
    b. the aqueous composition according to any of embodiments 15-17, wherein the aqueous composition is disposed over the first and/or second side(s) of the flexible substrate.

19. The dry wipe product according to embodiment 18, wherein the aqueous composition further comprises at least one additional ingredient selected from the group consisting of:
    a. a natural oil or a natural butter;
    b. a fragrance; and
    c. a conditioning agent,
wherein the at least one additional ingredient is biodegradable.

20. The dry wipe product according to embodiment 18 or 19, wherein the flexible substrate is rectangular and has a first dimension that is about 2 inches to about 6.4 inches and a second dimension that is about 4 inches to about 9 inches.

21. The dry wipe product according to embodiment 20, wherein the flexible substrate has a first dimension that is about 2 inches and a second dimension that is about 4 inches.

22. The dry wipe product according to embodiment 20, wherein the flexible substrate has a first dimension that is about 6.4 inches and a second dimension that is about 9 inches.

23. The dry wipe product according to any of embodiments 18-22, wherein the flexible substrate is a wood-fiber sheet.

24. The dry wipe product according to any of embodiments 18-23, wherein a total amount of about 0.1 grams to about 1.5 grams of the aqueous composition is disposed on the first and/or second sides of the flexible substrate.

25. A method of reducing frizz, reducing static and/or increasing shine on hair comprising wiping the hair with the dry wipe product according to any of embodiments 18-24, wherein the hair is wiped with a side of the dry wipe product having the aqueous composition disposed thereon.

26. A method of making the dry wipe product according to any of embodiments 18-24, comprising:
    a. spraying the aqueous composition onto the first and/or second side(s) of the flexible substrate; and
    b. drying the flexible substrate.

27. A method of making the dry wipe product according to any of embodiments 18-24, comprising:
    a. submerging the first side and/or second side of the flexible substrate in the aqueous composition;
    b. removing the flexible substrate from the aqueous composition; and
    c. drying the flexible substrate.

28. A method of reducing frizz, reducing static and/or increasing shine on hair comprising providing a dry wipe product comprising:
    a. a flexible substrate having a first side and a second side; and
    b. an anhydrous composition comprising:
        i. at least one wax; and
        ii. a solvent comprising a fatty ester and an ester oil,
wherein the anhydrous composition is disposed on the first and/or second side(s) of the flexible substrate, and wherein the method further comprises wiping the hair with a side of the dry wipe product having the anhydrous composition disposed thereon.

29. The method according to embodiment 28, wherein the dry wipe product is biodegradable.

30. The method according to embodiment 28 or 29, wherein the anhydrous composition is biodegradable.

31. A method of reducing frizz, reducing static and/or increasing shine on hair comprising providing a dry wipe product comprising:
    a. a flexible substrate having a first side and a second side; and
    b. an aqueous composition comprising:
        i. water;
        ii. a polysaccharide;
        iii. a sugar;
        iv. a fatty alcohol;
        v. a cationic surfactant; and
        vi. at least one natural oil;
wherein the aqueous composition is disposed on the first and/or second side(s) of the flexible substrate, and wherein the method further comprises wiping the hair with a side of the dry wipe product having the aqueous composition disposed thereon.

32. The method according to embodiment 31, wherein the dry wipe product is biodegradable.

33. The method according to embodiment 31 or 32, wherein the flexible substrate is biodegradable.

34. The method according to any of embodiments 31-33, wherein the aqueous composition is biodegradable.

35. A dry wipe product comprising:
    a. a flexible substrate having a first side and a second side; and
    b. an anhydrous composition, wherein the anhydrous composition comprises:
i. at least one wax; and
ii. a solvent comprising a fatty ester and an ester oil; and
iii. optionally, a second wax,
and further wherein the anhydrous composition is disposed on the first and/or second side(s) of the flexible substrate.

36. The dry wipe product of embodiment 35, wherein said at least one wax consists essentially of ozokerite.

37. The dry wipe product according to embodiment 35 or 36, wherein the fatty ester is isopropyl palmitate and the ester oil is caprylic/capric triglyceride.

38. The dry wipe product according to any of embodiments 35-37, wherein the second wax is selected from the group consisting of bayberry, jasmine wax, *mimosa* wax, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, ethylene homo- or copolymers, stearoxy dimethicone, dimethicone behenate, stearyl dimethicone, synthetic homo- and copolymer waxes, and mixtures thereof.

39. The dry wipe product according to any of embodiments 35-38, wherein the anhydrous composition comprises:
i. from about 5 wt. % to about 15 wt. % ozokerite;
ii. from about 10 wt. % to about 25 wt. % of a fatty ester; and
iii. from about 15 wt. % to about 35 wt. % of an ester oil; and
iv. optionally, a second wax.

40. The dry wipe product according to any of embodiments 35-39, wherein the anhydrous composition, the flexible substrate or both is or are biodegradable.

41. A method of making the dry wipe product according to any of embodiments 35-40, comprising:
a. melting the anhydrous composition;
b. applying the melted anhydrous composition to the first and/or second side(s) of the flexible substrate; and
c. cooling the anhydrous composition.

42. A dry wipe product comprising:
a. a flexible substrate having a first side and a second side; and
b. an aqueous composition,
wherein the aqueous composition comprises:
i. water;
ii. a polysaccharide;
iii. a sugar;
iv. a fatty alcohol;
v. a cationic surfactant; and
vi. at least one natural oil,
and further wherein the aqueous composition is disposed on the first and/or second side(s) of the flexible substrate.

43. The dry wipe product according to embodiment 42, wherein aqueous composition comprises:
i. water;
ii. from about 0.01 wt. % to about 1 wt. % of a polysaccharide;
iii. from about 0.01 wt. % to about 1 wt. % of a sugar;
iv. a fatty alcohol;
v. a cationic surfactant; and
vi. from about 0.001 wt. % to about 0.010 wt. % of at least one natural oil.

44. The dry wipe product according to embodiment 42 or 43, wherein the polysaccharide is carageenan and the sugar is glucose.

45. The dry wipe product according to any of embodiments 42-44, wherein the fatty alcohol is cetearyl alcohol and the cationic surfactant is dipalmitoylethyl hydroxyethylmonium methosulfate.

46. The dry wipe product according to any of embodiments 35-40 or 42-45, wherein the anhydrous composition or the aqueous composition further comprises at least one additional ingredient selected from the group consisting of:
a. a natural oil or a natural butter;
b. a fragrance; and
c. a conditioning agent,
wherein the at least one additional ingredient is biodegradable.

47. The dry wipe product according to any of embodiments 42-46, wherein the flexible substrate, the aqueous composition or both is or are biodegradable.

48. A method of reducing frizz, reducing static and/or increasing shine on hair comprising wiping the hair with the dry wipe product according to any of embodiments 35-40 or 42-47, wherein the hair is wiped with a side of the dry wipe product having either the anhydrous composition or the aqueous composition disposed thereon.

49. A method of making the dry wipe product according to any of embodiments 42-47, comprising either:
A) i. spraying the aqueous composition onto the first and/or second side(s) of the flexible substrate; and
ii. drying the flexible substrate; or
B) i. submerging the first side and/or second side of the flexible substrate in the aqueous composition;
ii. removing the flexible substrate from the aqueous composition; and
iii. drying the flexible substrate.

50. The dry wipe product according to any of embodiments 35-40 or 42-47, wherein the flexible substrate is rectangular and has a first dimension that is at least about 2 inches to about 6.4 inches and a second dimension that is at least about 4 inches to about 9 inches.

51. The dry wipe product according to embodiment 50, wherein the first dimension of the flexible substrate is about 2 inches and the second dimension of the flexible substrate is about 4 inches.

52. The dry wipe product according to embodiment 50, wherein the first dimension of the flexible substrate is about 6.4 inches and the second dimension of the flexible substrate is about 9 inches.

53. The dry wipe product according to any of embodiments 35-40 or 42-47, wherein the flexible substrate is a wood-fiber sheet.

54. The dry wipe product according to any of embodiments 35-40 or 50-53, wherein a total amount of about 0.1 grams to about 1.5 grams of the anhydrous composition is disposed on the first and/or second side(s) of the flexible substrate.

55. The dry wipe product according to any of embodiments 42-47 or 50-53, wherein a total amount of about 0.1 grams to about 1.5 grams of the aqueous composition is disposed on the first and/or second side(s) of the flexible substrate.

56. The dry wipe product according to any of embodiments 35-40, 42-47 or 50-55, wherein the dry wipe product is biodegradable.

57. The method according to any of embodiments 41, 48 or 49, wherein the dry wipe product is biodegradable.

58. The method according to any of embodiments 41, 48 or 49, wherein the flexible substrate is rectangular and has a first dimension that is at least about 2 inches to about 6.4 inches and a second dimension that is at least about 4 inches to about 9 inches.

59. The method according to embodiment 58, wherein the first dimension of the flexible substrate is about 2 inches and the second dimension of the flexible substrate is about 4 inches.

60. The method according to embodiment 58, wherein the first dimension of the flexible substrate is about 6.4 inches and the second dimension of the flexible substrate is about 9 inches.

61. The method according to any of embodiments 41, 48 or 49, wherein the flexible substrate is a wood-fiber sheet.

62. The method according to any of embodiments 41, 48 or 49, wherein a total amount of about 0.1 grams to about 1.5 grams of the anhydrous composition or the aqueous composition is disposed on the first and/or second side(s) of the flexible substrate.

The foregoing description or disclosure illustrates and describes the present invention. Additionally, the disclosure shows and describes many of the preferred embodiments of the invention, but, as mentioned above, it is to be understood that changes or modifications within the scope of the concept as expressed herein, commensurate with the above teachings and/or skill or knowledge of the relevant art, can be made to the disclosed embodiments while still remaining within the broad concept of the present invention. The embodiments described hereinabove are further intended to explain best modes known of practicing the invention and to enable others skilled in the art to utilize the disclosure in such, or other, embodiments and with the various modifications required by the particular applications or uses disclosed herein. Accordingly, the description is not intended to limit the invention to the form disclosed herein. Also, it is intended that the appended claims be construed to include alternative embodiments.

What is claimed is:

1. A dry wipe product consisting of:
   a. a flexible substrate having a first side and a second side; and
   b. an anhydrous composition disposed on the first and/or second side(s) of the flexible substrate, the anhydrous composition consisting of:
      i. from about 5 wt. % to about 15 wt. % ozokerite;
      ii. from greater than 0 wt. % to about 50 wt. % of a fatty ester obtained from a linear or branched chain, saturated, or unsaturated alcohol having from 1 to 24 carbon atoms and a linear or branched chain fatty acid having from 3 to 24 carbon atoms;
      iii. from about 15 wt. % to about 35 wt. % of an ester oil selected from the group consisting of a mono-, di- or tri-ester of glycerol;
      iv. a second wax;
      v. one or more natural oils and/or natural butters;
      vi. optionally, one or more polyols;
      vii. optionally, one or more solid fatty alcohols;
      viii. optionally, one or more amidoamines;
      ix. optionally, one or more emulsifiers;
      x. optionally, one or more conditioning agents; and
      xi. optionally, one or more fragrances.

2. The dry wipe product of claim 1, wherein the second wax is beeswax.

3. The dry wipe product according to claim 1, wherein the fatty ester is isopropyl palmitate and the ester oil is caprylic/capric triglyceride.

4. The dry wipe product according to claim 1, wherein the second wax is bayberry wax, jasmine wax, *mimosa* wax, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, ethylene homo- or copolymers, stearoxy dimethicone, dimethicone behenate, stearyl dimethicone, synthetic homo- and copolymer waxes, or a mixture thereof.

5. The dry wipe product according to claim 1, wherein the anhydrous composition, the flexible substrate or both is or are biodegradable.

6. The dry wipe product of claim 1, wherein the fatty ester is isopropyl palmitate.

7. The dry wipe product of claim 1, wherein the ester oil is a glyceride fatty ester derived from peanut oil, sesame oil, avocado oil, coconut oil, cocoa butter, almond oil, safflower oil, corn oil, cotton seed oil, castor oil, hydrogenated castor oil, olive oil, jojoba oil, palm oil, soybean oil, wheat germ oil, linseed oil, or sunflower seed.

8. The dry wipe product of claim 1, wherein the ester oil is caprylic/capric triglyceride.

9. The dry wipe product of claim 1, wherein the flexible substrate is a wood fiber sheet.

10. The dry wipe product according to claim 1, wherein the natural oil is camellina oil, maringa oil, argan oil, lavendar oil, sweet almond oil, avocado oil, castor oil, olive oil, jojoba oil, sunflower oil, wheatgerm oil, sesame oil, groundnut oil, grapeseed oil, soybean oil, rapeseed oil, safflower oil, coconut oil, corn oil, hazelnut oil, shea butter, palm oil, apricot kernel oil, or beauty-leaf oil.

11. The dry wipe product according to claim 1, wherein the anhydrous composition incorporates the one or more fragrances.

12. The dry wipe product according to claim 1, wherein the anhydrous composition incorporates the one or more conditioning agents.

13. The dry wipe product according to claim 1, wherein the fatty ester is dicaprylyl carbonate.

14. The dry wipe product according to claim 1, wherein the fatty ester diisopropyl adipate.

15. The dry wipe product according to claim 1, wherein the fatty ester is isopropyl palmitate, dicaprylyl carbonate, and diisopropyl adipate.

* * * * *